(12) United States Patent
Märzendorfer et al.

(10) Patent No.: US 9,684,045 B2
(45) Date of Patent: Jun. 20, 2017

(54) IMAGING THE TEETH BY MEANS OF MAGNETIC RESONANCE TECHNOLOGY WITH NON-UNIQUE GRADIENTS

(71) Applicants: Walter Märzendorfer, Erlangen (DE); Sebastian Schmidt, Weisendorf (DE)

(72) Inventors: Walter Märzendorfer, Erlangen (DE); Sebastian Schmidt, Weisendorf (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 839 days.

(21) Appl. No.: 14/034,936

(22) Filed: Sep. 24, 2013

(65) Prior Publication Data
US 2014/0084920 A1 Mar. 27, 2014

(30) Foreign Application Priority Data
Sep. 26, 2012 (DE) .................. 10 2012 217 459

(51) Int. Cl.
| G01R 33/385 | (2006.01) |
| A61B 5/055 | (2006.01) |
| G01R 33/44 | (2006.01) |
| A61B 5/00 | (2006.01) |

(52) U.S. Cl.
CPC ............ *G01R 33/385* (2013.01); *A61B 5/004* (2013.01); *A61B 5/055* (2013.01); *A61B 5/0555* (2013.01); *A61B 5/4547* (2013.01); *G01R 33/445* (2013.01)

(58) Field of Classification Search
CPC ....... A61B 5/004; A61B 5/055; A61B 5/0555; A61B 5/4547; G01R 33/445
See application file for complete search history.

(56) References Cited

U.S. PATENT DOCUMENTS

| 5,185,576 | A | 2/1993 | Vavrek | |
|---|---|---|---|---|
| 5,304,933 | A | 4/1994 | Vavrek | |
| 8,847,597 | B2 * | 9/2014 | Rasche | G01R 33/421 324/318 |
| 2009/0128148 | A1 * | 5/2009 | Hennig | G01R 33/48 324/309 |
| 2012/0223711 | A1 * | 9/2012 | Weinberg | G01R 33/3852 324/309 |
| 2013/0136329 | A1 * | 5/2013 | Tao | A61B 5/0037 382/131 |

FOREIGN PATENT DOCUMENTS

| DE | 102009020361 A1 | 11/2010 |
| DE | 102009027119 A1 | 12/2010 |
| DE | 102011007501 B3 | 5/2012 |

OTHER PUBLICATIONS

J Hennig et al "PatLoc Imaging in non-bijective, curvilinear magnetic field gradients", Proc Intl Soc Magn Res 15, p. 453, 2007, 2007.
Dennis L Parker "Multiple-Region Gradient Arrays for Extended Field of View, Increased Performance, and Reduced Nerve Stimulation in Magnetic Resonance Imaging", MRM 56, pp. 1251-1260, 2006, 2006.

* cited by examiner

*Primary Examiner* — Gregory H Curran

(57) ABSTRACT

A gradient system according to the invention generates three superimposed gradient fields of which at least one of the three gradient fields is not unique in space (i.e. not bijective) and at least one of the three gradient has areas of the same field strength, which extend in parallel or orthogonally to a approximately U-shaped center plane of the teeth of one jaw of a patient.

11 Claims, 5 Drawing Sheets

IMAGING THE TEETH BY MEANS OF MAGNETIC RESONANCE TECHNOLOGY WITH NON-UNIQUE GRADIENTS

CROSS REFERENCE TO RELATED APPLICATIONS

The present application claims priority to German Patent Office application No. 10 2012 217 459.1 EP filed Sep. 26, 2012, the entire content of which is hereby incorporated herein by reference.

FIELD OF INVENTION

A gradient system for imaging the teeth, a method for generating magnetic resonance data on a patient's teeth in a selected region, a magnetic resonance system, and a non-transitory computer readable medium are disclosed.

BACKGROUND OF INVENTION

Diseases of the teeth and of the periodontium, such as, for example, caries or periodontosis are nowadays usually diagnosed with X-ray-based imaging methods. Here, either conventional or so-called digital X-rays are used with projection methods or recently also three-dimensional (3D) methods, such as, for example, digital volume tomography (DVT), a type of X-ray computed tomography of the teeth and the viscerocranium.

However, for many dental diseases, a magnetic resonance imaging (MRI) examination would be the better alternative since it operates without ionizing radiation and enables a better representation of soft-tissue contrasts.

Magnetic resonance technology is a known technology which can be used to generate images of the interior of an object under examination. In simplified terms, for this purpose, the object under examination is positioned in a magnetic resonance device in a comparatively strong static, homogeneous basic magnetic field, also known as the $B_0$ field with field strengths of 0.2 tesla to 7 tesla and more so that the nuclear spins of the object orient along the basic magnetic field. To trigger nuclear spin resonances, high-frequency excitation pulses (HF pulses) are irradiated into the object under examination, the triggered nuclear spin resonances are measured as so-called k-space data and used as the basis for the reconstruction of MR images or the determination of spectroscopy data. For spatial encoding of the measured data, rapidly switched magnetic gradient fields are superimposed on the basic magnetic field. The recorded measured data is digitized and stored in a k-space matrix as complex values. An associated MR image can be reconstructed from the k-space matrix populated with such values, for example by means of a multidimensional Fourier transformation.

However, an MRI system for dental medicine has to meet relatively high requirements for image quality, since the structures depicted are very small. In order, for example, to identify caries lesions, spatial resolutions of much smaller than a millimeter are required. At the same time, it is necessary for many questions (for example, an evaluation of the strength or porosity of the jaw bone) to represent bound protons, which in turn requires measurements with extremely short echo times, so-called "ultra-short TE". However, this places high requirements on the steepness of the gradient fields since the phase difference of the spins only develops quickly enough with very steep gradients. In the case of a conventional MR system with a large field of view (FOV), this results in very high gradient amplitudes, which are either biologically impossible due to stimulation effects or would at least require an extremely expensive gradient system which is not economically viable for use in dental imaging.

Already known are intraoral receiver coils which are arranged in the patient's mouth and hence are very close to the target region and thus result in an improved signal-to-noise-ratio (SNR) compared to receiver coils arranged in more remote locations. Also known are dedicated head scanners for the head with a small field-of-view which only encompass the patient's head. However, nowadays these are mainly used for examinations of the brain.

Also known, for example from the article by Hennig et al.: "PatLoc: Imaging in non-bijective, curvilinear magnetic field gradients", Proc. Intl. Soc. Magn. Res. 15, page 453, 2007 and the article by Parker et al.: "Multiple-Region Gradient Arrays for Extended Field of View, Increased Performance, and Reduced Nerve Stimulation in Magnetic Resonance Imaging"; MRM 56; pages 1251-1260, 2006, are MRI methods, which use non-unique field gradients of the gradient fields. Here, the gradient fields generated are not unique and can also be curved. The unique assignment of the signals to the positions is performed with the aid of the known illumination profiles of the coils used. These techniques are known by the name "PatLoc". However, one drawback with these methods is the fact that there are positions at which the imaging cannot be performed at all or can only be performed with great difficulty, namely the zero positions of the gradients. Hitherto, techniques of this kind have been used for imaging of the brain, where for certain questions it is possible to dispense with precise imaging of the center of the brain and importance is above all attached to the high-resolution representation of the cerebral cortex (neocortex) such as is, for example, described in the aforementioned article by Hennig et al.

Also known from DE 10 2009 020 361 A1 is the use of non-unique gradients in the imaging the female breast.

SUMMARY OF INVENTION

The invention is based on the object of disclosing a gradient system, a method, a magnetic resonance system, and a non-transitory computer readable medium which permit a representation of the teeth and the jaw in high resolution and at high speed.

The object is achieved by a gradient system, a method, a magnetic resonance system, and a non-transitory computer readable medium.

A gradient system according to the invention generates three superimposed gradient fields ($G_1$, $G_2$, $G_3$), of which at least one of the three gradient fields ($G_1$, $G_2$, $G_3$) is not unique (i.e. not bijective) in space and at least one of the three gradient fields ($G_1$, $G_2$, $G_3$) has areas of the same field strength, which extend in parallel or orthogonally to an approximately U-shaped center plane of the teeth of a jaw (ZK) of a patient (P).

The local gradient fields generated with the gradient system can be embodied more steeply than is the case with conventional gradient field systems and also switched more rapidly without reaching the stimulation limits (for example SAR) which restrict the steepness of the gradient fields, since the amplitudes of the gradient fields generated by a gradient system according to the invention are comparatively low. The particularly steep gradient fields are particularly suitable for MR imaging sequences which enable extremely short echo times (UTE sequences) in order to develop the phase differences between the spins in the short time, in which, for example, signals from teeth or (jaw) bones relax. This makes the gradient fields generated by means of a gradient system according to the invention particularly suitable for dental imaging.

At the same time, the power required to generate the gradient fields by means of the gradient system according to the invention during the switching of the gradient fields is very low since the spatial distance to the target region, the teeth, is very small due to the close proximity. This advantageously results in low requirements for the necessary electrical power consumption, the cooling, the conductor material etc.

The embodiment of at least one gradient field such that its areas of the same field strength extend in parallel or orthogonal to the approximately U-shaped center plane of the teeth of a patient's jaw facilitates the simple generation of images of layers and hence sectional images parallel to the center plane of the teeth.

Hence, a gradient system according to the invention provides a particularly efficient MR system for the special purpose of dental imaging and at the same time is inexpensive to produce.

A method according to the invention for generating magnetic resonance data on the teeth of a patient in a selected region comprises:
  irradiation of at least one high-frequency pulse into the selected region,
  reading out measuring signals generated,
  during the irradiation of the at least one high-frequency pulse and the reading-out the measuring signals, switching of gradient fields for spatial encoding, wherein the irradiated gradient fields are at least partially generated by means of a gradient system so that at least one of the gradient fields is not spatially unique (i.e. not bijective),
  storing the read-out measuring signals as magnetic resonance data,
  processing the magnetic resonance data obtained to form an image data set and
  displaying and/or storing the image data set obtained from the processing of the magnetic resonance data.

A method according to the invention enables the particularly cost-effective and at the same time particularly efficient excitation and measurement of measuring signals from teeth for the imaging.

A magnetic resonance system according to the invention for acquiring magnetic resonance data in a selected region within an object under examination comprises a basic magnet, a gradient system according to the invention as described herein, at least one HF antenna and a control mechanism for controlling the gradient system and the at least one HF antenna, for receiving the measuring signals received by the at least one HF antenna and for evaluating the measuring signals and for creating the magnetic resonance data.

In particular, the magnetic resonance system is embodied such that it generates magnetic resonance data on the teeth of a patient in the selected region, wherein the magnetic resonance system irradiates at least one high-frequency pulse into the selected region, reads out generated measuring signals, during the irradiation of the at least one high-frequency pulse and the reading-out of the measuring signals, switches gradient fields for spatial encoding, wherein the irradiated gradient fields are at least partially generated by means of a gradient system according to the invention described herein so that at least one of the gradient fields is not spatially unique (i.e. not bijective), stores the read-out measuring signals as magnetic resonance data, processes the magnetic resonance data obtained to form an image data set and stores and/or displays the image data set obtained from the processing of the magnetic resonance data.

A non-transitory computer readable medium includes the instructions stored theron so that when the instructions are executed on a computing device the method is performed A non-transitory computer readable medium having instructions stored theron and that are executable by a computing device, the instructions performing the method as described herein.

The advantages and embodiments disclosed with respect to the gradient system and the method also apply analogously for the magnetic resonance system, the computer program product and the electronically readable data carrier.

BRIEF DESCRIPTION OF THE DRAWINGS

Further advantages and details of the present invention may be derived from the exemplary embodiments described in the following and with reference to the drawings. The examples described do not represent a restriction of the invention. The figures show.

DETAILED DESCRIPTION OF INVENTION

Figure 1:
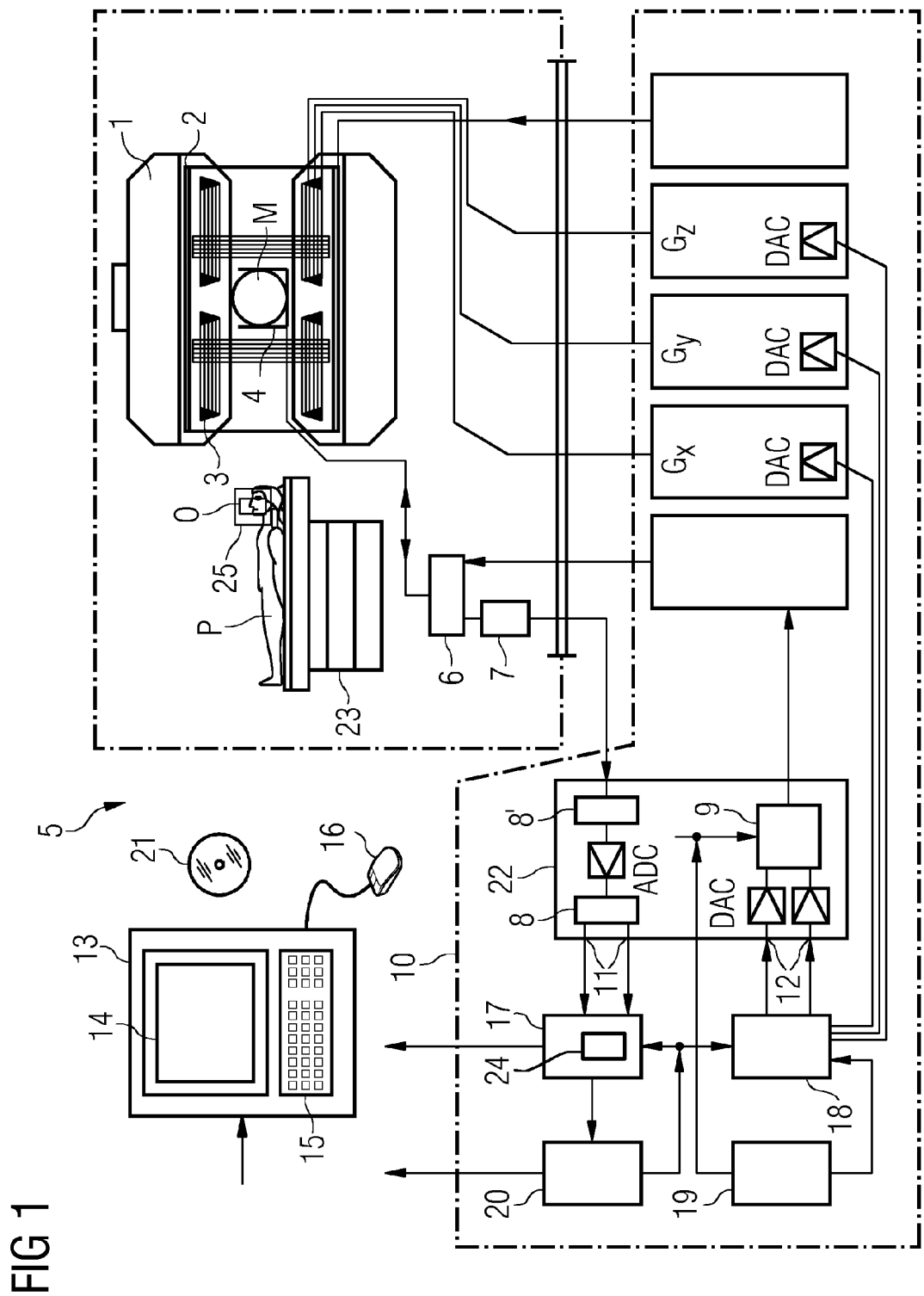
FIG. 1 a schematic view of a magnetic resonance system according to the invention, FIG. 2 a schematic representation of the course of the areas of same field strength of a gradient field generated by a gradient system according to the invention, FIG. 3 a schematic representation of a possible course of the field strength of the gradient field from FIG. 2 in one direction, FIG. 4 a schematic representation of the course of the areas of same field strength of a further gradient field generated by a gradient system according to the invention, FIG. 5 a schematic representation of a possible course of the field strength of the gradient field from FIG. 4, FIG. 6 a schematic representation of the course of the areas of same field strength of a further gradient field generated by a gradient system according to the invention, FIG. 7 a schematic representation of a possible course of the field strength of the gradient field from FIG. 6 in one direction, FIG. 8 a schematic representation of a gradient system according to the invention and FIG. 9 a schematic flow diagram of a method according to the invention for generating magnetic resonance data on the teeth of a patient in a selected region.

FIG. 1 is a schematic representation of a magnetic resonance system 5 (a magnetic-resonance imaging or nuclear spin tomography device). Here, a basic field magnet 1 generates a temporally constant strong magnetic field for the polarization or alignment of the nuclear spins in a selected region O of a patient P, including teeth of the patient P, who is to be examined while lying on a table 23 in the magnetic resonance system 5. The high homogeneity of the basic magnetic field necessary for the nuclear magnetic resonance measurement is defined in a typically, but not mandatorily, spherical measurement volume M in which the parts of the human body to be examined are arranged. To support the homogeneity requirements and in particular to eliminate temporally invariable influences, so-called shim plates made from ferromagnetic material are mounted at a suitable location. Temporally variable influences are eliminated by shim coils 2.

A cylindrical gradient coil system 3 comprising three sub-windings is typically inserted in the basic magnet 1. Each sub-winding is supplied with current by an amplifier for generating a, for example, linear (also temporally variable) gradient field in the respective direction of the Cartesian coordinate system. Here, the first sub-winding of the gradient field system 3 generates a gradient $G_x$ in the x-direction, the second sub-winding a gradient $G_y$ in the y-direction and the third sub-winding a gradient $G_z$ in the z-direction. The amplifier comprises a digital-analog converter which is driven by a sequence controller 18 for the temporally correct generation of gradient pulses.

Typically one (or more) high-frequency antennas 4 are located within the gradient field system 3, in particular at least one multi-channel HF transmitter coil and at least one HF receiver coil, which converts the high-frequency pulses emitted by a high-frequency power amplifier into an alternating magnetic field for the excitation of the nuclei and alignment of the nuclear spins from the region O selected for examination of the patient P. Here, each high-frequency antenna 4 typically comprises one or more HF transmitter coils and one or more HF receiver coils in the form of a ring-shaped preferably linear or matrix-shaped arrangement of component coils. The HF receiver coils of the respective high-frequency antenna 4 also convert the alternating field emanating from the preceding nuclear spins, i.e. as a rule, the spin echo signals produced from a pulse sequence comprising one or more high-frequency pulses and one or more gradient pulses, into a voltage (measuring signal), which is supplied via an amplifier 7 to a high-frequency receive channel 8 of a high-frequency system 22. The high-frequency system 22 also comprises a transmission channel 9 in which the high-frequency pulses for the excitation of the nuclear magnetic resonance are generated. Here, the respective high-frequency pulses are displayed digitally as a sequence of complex numbers specified in the sequence controller 18 on the basis of a pulse sequence specified by the system computer 20 comprising at least one high-frequency pulse. This sequence of numbers is supplied as a real and imaginary part via in each case an input 12 to a digital-analog converter in the high-frequency system 22 and from there to a transmission channel 9. In the transmission channel 9, the pulse sequences are modulated on a high-frequency carrier signal having a base frequency corresponding to the mid-frequency.

The switch from transmission to reception mode is performed, for example, via a transmitter-receiver duplexer 6. The HF transmitter coils of the high-frequency antenna(s) 4 emit(s) the high-frequency pulses for the excitation of the nuclear spins into the measurement volume M and samples the resultant echo signals via the HF receiver coil(s). The correspondingly acquired magnetic resonance signals are phase-sensitively demodulated in the receive channel 8' (first demodulator) of the high-frequency system 22 to an intermediate frequency and digitized in the analog-digital converter (ADC). This signal is again demodulated to the frequency 0. Demodulation to the frequency 0 and the separation into a real and imaginary part takes place after the digitization in the digital domain in a second demodulator 8. An image converter 17 can be used to reconstruct an MR image or image data set from the magnetic resonance data acquired in this way. To this end, the image converter 17 comprises in particular a processing unit 24, with which recorded magnetic resonance data can be processed to form an image data set. The administration of the measured magnetic resonance data, the image data and the control programs is performed via the system computer 20. On the basis of specification with control programs, the sequence controller 18 controls the generation of the respectively desired pulse sequences and the corresponding sampling of the k-space. Here, in particular, the sequence controller 18 controls the temporally correct switching of the gradient fields, the emission of the high-frequency pulses with a defined phase amplitude and the reception of the nuclear magnetic resonance signals.

In any case, the magnetic resonance device 5 comprises a gradient system according to the invention 25, which can be arranged around the jaw of the patient P and is also connected to the above-mentioned amplifiers for supplying the gradient coils of the gradient system 25 and the system computer 20 and optionally to said high-frequency power amplifier and the high-frequency system 22 for driving high-frequency antennas of the gradient system 25 (not shown).

The time basis for the high-frequency system 22 and the sequence controller 18 is made available by a synthesizer 19. The selection of corresponding control programs for generating a recording of magnetic resonance data, which is stored, for example, on a DVD 21, the selection of a selected region O, which is to be excited and received from the magnetic resonance data and the representation of a generated MR image take place, for example, via a terminal 13 comprising a keyboard 15, a mouse 16 and a screen 14, with which for example the selected region O can be input.

Figure 2:
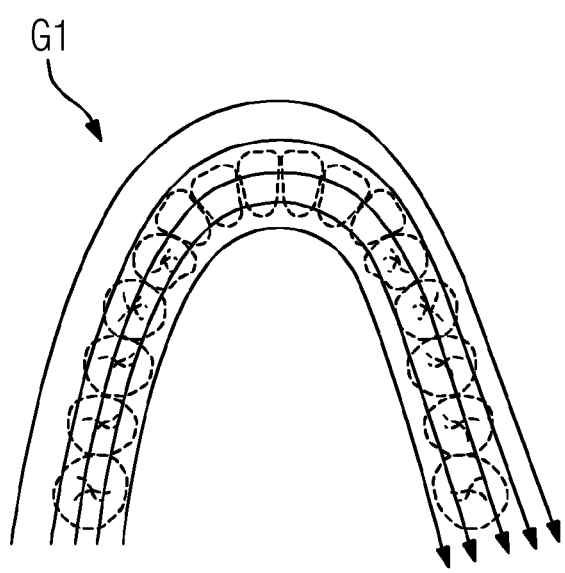

FIG. 2 shows a schematic representation of the course of the areas of same field strength of a gradient field generated by a gradient system according to the invention G1. As is evident from the exemplary jaw indicated by the dashed line in the background, the areas of same field strength shown as lines extend in parallel to the center plane of the teeth of the jaw in a transversal plane. The center plane of the teeth does not extend in a shape of this kind, which could be approximately described as U-shaped, in all patients. In particular following traumatic impacts on the jaw, the center plane can be severely deformed and as a result the disclosed areas of the same field strength no longer always extend in parallel to a deformed center plane of this kind. However, the areas of same field strength at least extend in parallel to an average, shown here as approximately U-shaped, center plane of the teeth of a jaw. Exact parallelism with individual jaws is not necessary, but the local gradient field generated by the gradient system according to the invention generated should act on all teeth of the jaw to be examined or the region of a jaw to be examined.

Figure 3:
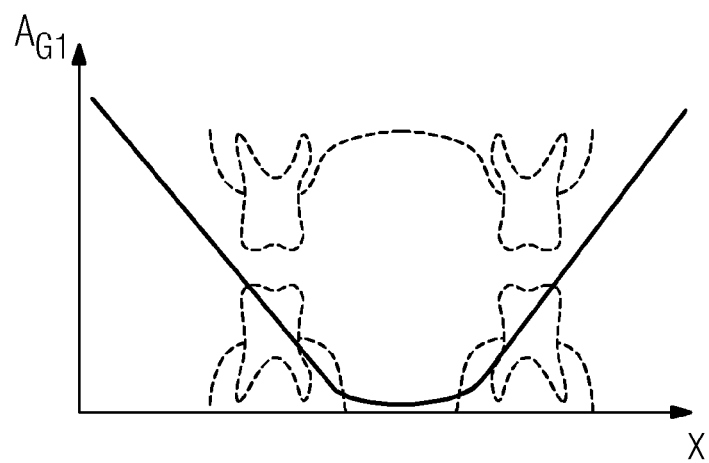

FIG. 3 shows a schematic representation of a possible course of the field strength $A_{G1}$ of the gradient field G1 from FIG. 2 in the x-direction in a coronal plane through the jaw. For purposes of illustration, here once again exemplary teeth are shown schematically with an indicated upper jaw (top) and lower jaw (bottom) by dashed lines. As can be seen, the gradient field G1 is not spatially unique in the direction shown since the same field strength occurs for at least two different x-coordinates. Hence, the assignment of x-coordinate to field strength is not bijective. At the same time, the region of the gradient field G1, in which its field strength does not vary spatially or only varies to a very low degree, lies in the center of the jaw where there are no teeth. Hence, although there is a zone present in the x-direction at which no, or only very restricted magnetic resonance measurements are possible with the gradient field G1, this is in a region which is of no interest for the examination of the teeth region between the left and the right teeth. On the other hand, a gradient field G1 of this kind enables a frequently desired representation in the style of an orthopantomograph (along the center line of the teeth) to be produced simply and with high image quality. Hence, a gradient system according to the invention enables a PatLoc measurement as mentioned above, wherein the drawbacks of this type of measurement can be neatly avoided by the arrangement of the gradient fields according to the invention.

Figure 4:
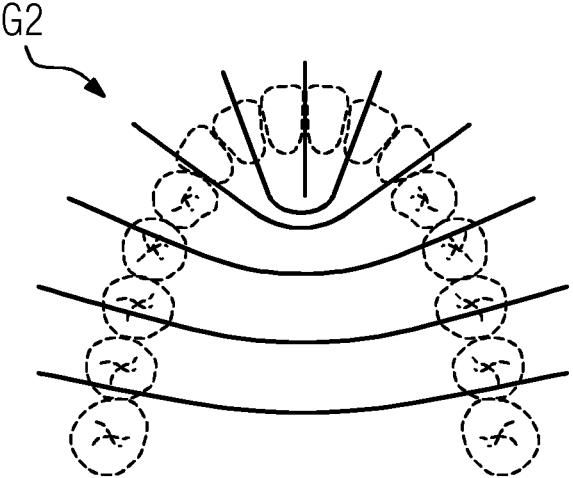

FIG. 4 shows a schematic representation of the course of the areas of same field strength of a further gradient field generated by a gradient system according to the invention G2. As can be identified by the jaw indicated by the dashed line in the background, the areas of same field strength shown as lines extend orthogonally to the center plane of the teeth of the jaw in a transversal plane. As already explained, the center plane of the teeth does not extend in a shape of this kind, which could be approximately described as U-shaped, in all patients. In particular following traumatic impacts on the jaw, the center plane can be severely deformed and as a result the disclosed areas of the same field strength no longer always extend orthogonally to a deformed center plane of this kind. However, the areas of same field strength at least extend orthogonally to an average, shown here as approximately U-shaped, center plane of the teeth of a jaw. Exact orthogonality to individual jaws is not necessary, but the local gradient field generated by the gradient system according to the invention generated should act on all teeth of the jaw to be examined or the region of a jaw to be examined.

Figure 5:
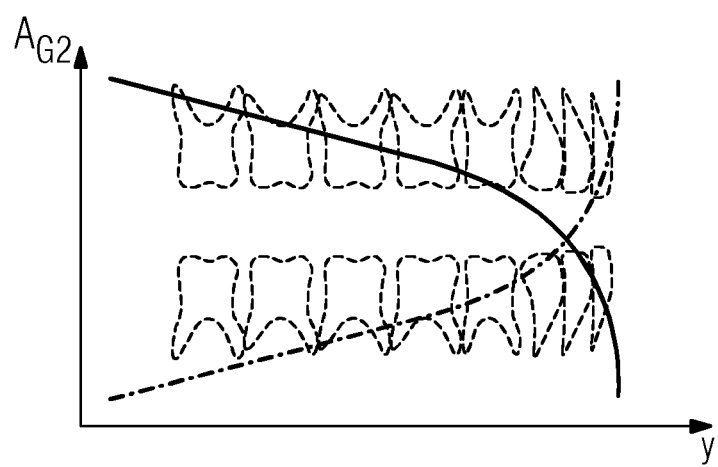

FIG. 5 shows schematic representations of a possible course of the field strength $A_{G2}$ of the gradient field G2 from FIG. 4 in the y-direction in a sagittal plane through the jaw. Two possible courses are shown. A first possible course is shown by a continuous line, a second possible course is shown by a dot-dash line. For purposes of illustration, here once again exemplary teeth are shown schematically with an indicated upper jaw (top) and lower jaw (bottom) by dashed lines. Here, the region of the gradient field G2, in which its field strength varies greatly in the y-direction lies within the region of the anterior teeth, which in the y-direction are narrower than the molars.

Figure 6:
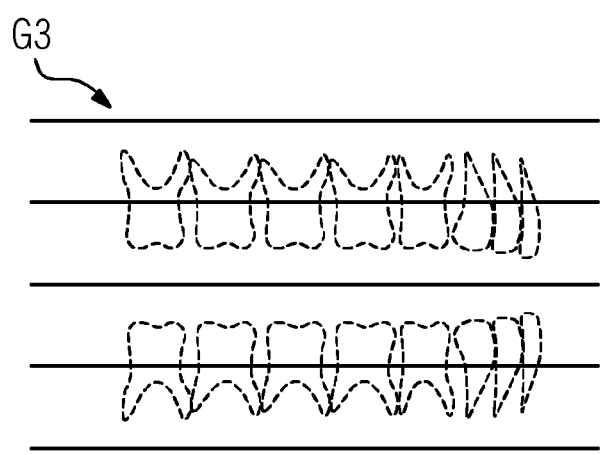

FIG. 6 shows a schematic representation of the course of the areas of same field strength of a further gradient field generated by a gradient system according to the invention G3. For purposes of illustration, exemplary teeth in a sagittal plane through the jaw are schematically indicated in the background. The areas of same field strength of the gradient field G3 extend in parallel to the transversal plane of the jaw of the patient.

Figure 7:
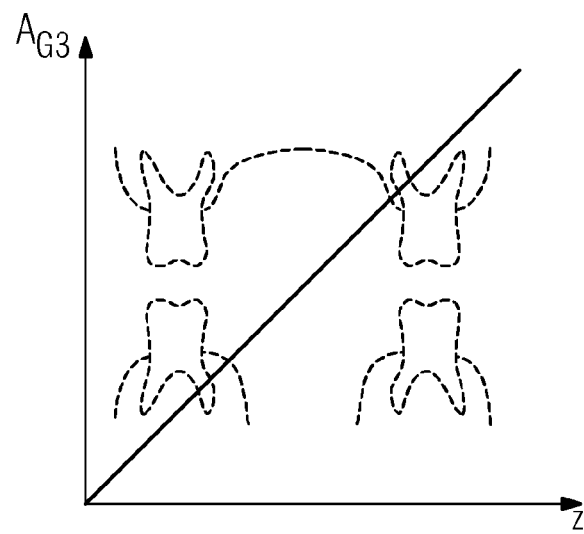

FIG. 7 is a schematic representation of a possible course of the field strength of the gradient field G3 from FIG. 6. This could simply be an otherwise typical linear course of the gradient field G3 in the z-direction. For purposes of illustration, once again teeth and jaw are shown in a coronal plane in the background.

Overall, with different embodiments of a gradient system according to the invention, non-unique gradient fields can be switched in one, two or even three spatial directions. If non-unique gradient fields are only in one or two spatial directions, the remaining two spatial directions or the remaining last spatial direction can be covered by unique, for example conventional linear, gradient fields.

In an exemplary embodiment, a first gradient field is switched such that the areas of same field strength of the first gradient field extend substantially in parallel to the center line of the teeth of the jaw to be examined, a second gradient field is switched such that the areas of same field strength of the first gradient field extend substantially orthogonally to the center line of the teeth of the jaw to be examined and a third gradient field is switched such that, for example in z-direction, along the patient, a conventional linear gradient field is generated in the region to be examined.

Here, the non-unique gradient fields can be used for both layer selection and phase encoding or frequency encoding during the measurement.

Figure 8:
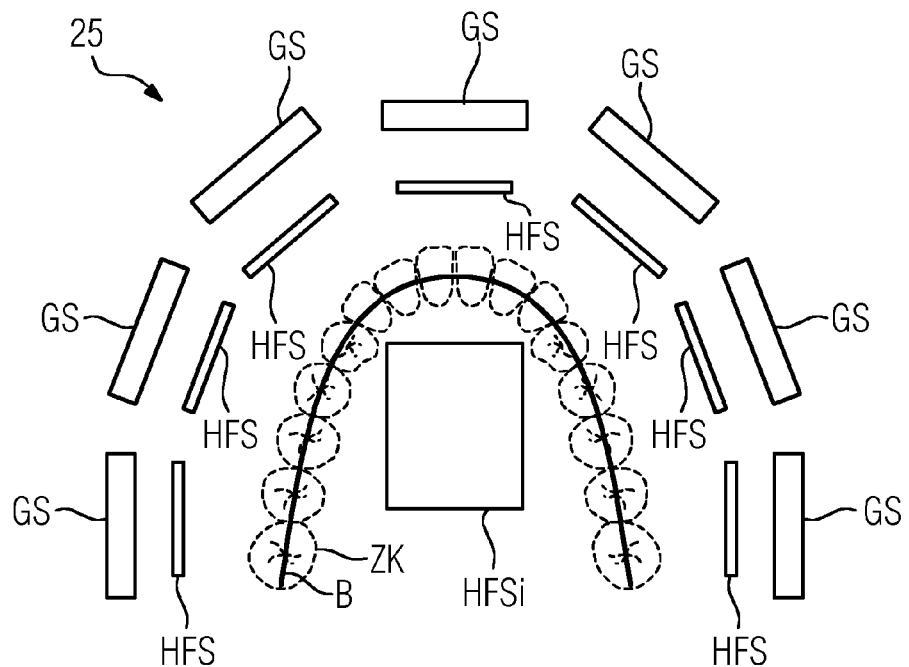

FIG. 8 is a schematic representation of a gradient system according to the invention 25.

The gradient system 25 comprises at least one gradient coil GS, which is embodied such that it can be arranged around the head of a patient around the jaw (ZK). Here, the gradient system is at the same time embodied such that it can be arranged in a measurement volume M of a magnetic resonance system 5 around the jaw of the patient (see FIG. 1) and there the magnetic resonance system 5 and the gradient system 25 can be used to obtain magnetic resonance data on the teeth of the patient when the magnetic resonance system 5 is in operation.

In the example shown, the gradient system 25 comprises seven gradient coils GS in the region around the jaw of the patient with which, in operation, optionally with the support of a further gradient field system 3 of the magnetic resonance system 5, at least one gradient field according to the invention is generated with areas of same field strength extending in parallel or orthogonally to the center plane of the teeth to be depicted (see FIGS. 2 and 4). Just one gradient field of this kind can be used to generate images of layers parallel to the center line of the teeth in a simple way. The way the gradient coils GS of the gradient system 25 are to be switched in order to generate gradient fields of this kind is, for example, described in the above-cited publication by Hennig et al. FIG. 8 shows, by way of example only, an arrangement of gradient coils GS and optionally high-frequency antennas HFS, HFSi in the region of the jaw ZK of the patient. Since no measurement of magnetic resonance data is performed in the region of the patient's neck, because no image data from this region is desired, the course of the areas of same field strength of the gradient fields and also the arrangement of further gradient coils and/or high-frequency antennas can to a large extent be freely set.

The gradient system 25 can be fixed on the head of the patient such that the gradient system is fixed relatively to the patient's jaw ZK. To this end, the gradient system 25 comprises, for example, a biting apparatus B on which the patient bites to fix the gradient system relatively to the jaw ZK. Here, after biting, the fixing should establish contact between the biting apparatus B and the jaw ZK at at least three points of which ideally one should be arranged in the left half of the jaw ZK, one in the right half of the jaw ZK and one in the anterior region of incisors of the jaw ZK. The remaining components of the gradient system 25 are rigidly connected to the biting apparatus so that reliable fixing is possible.

In one exemplary embodiment, the gradient system 25 comprises at least two high-frequency antennas HFS, HFSi, by means of which measuring signals from the region of the teeth of the jaw ZK can be received locally. Optionally, the high-frequency antennas are also suitable for the emission of high-frequency pulses. In this case, the high-frequency antennas HFS, HFSi can be embodied as either transmit-and-receive antennas or as individual high-frequency antennas HFS, HFSi for transmission and other high-frequency antennas HFS, HFSi for transmission.

The fact that the high-frequency antennas are to be arranged locally and hence close to the region of the teeth from which measuring signals are to be received results in very good reconstructability of the images in image data, in particular the signal-to-noise ratio (SNR) is particularly low.

The number of receive high-frequency antennas is, for example, at least 2, but advantageously more, for example between four and eight.

In one exemplary embodiment of the gradient system 25, at least one of the high-frequency antennas HFS is arranged between the at least one gradient coil GS of the gradient system 25 which can be arranged around the jaw (ZK) and the jaw (ZK) of the patient (P). This means that the high-frequency antennas HFS are only a short distance from the teeth from which measuring signals are to be received thus ensuring good signal quality. At the same time, there is more space outside the patient's mouth and hence more freedom with the arrangement of the high-frequency antennas HFS than there is, for example, inside the oral cavity.

In a further exemplary embodiment of the gradient system 25, additionally or alternatively at least one of the high-frequency antennas (HFSi) is arranged intraorally, in the interior of the jaw (ZK), i.e. within the oral cavity of the patient (P). Intraoral high-frequency antennas of this kind can be arranged particularly close to the target region from which measuring signals are to be excited and received.

Figure 9:
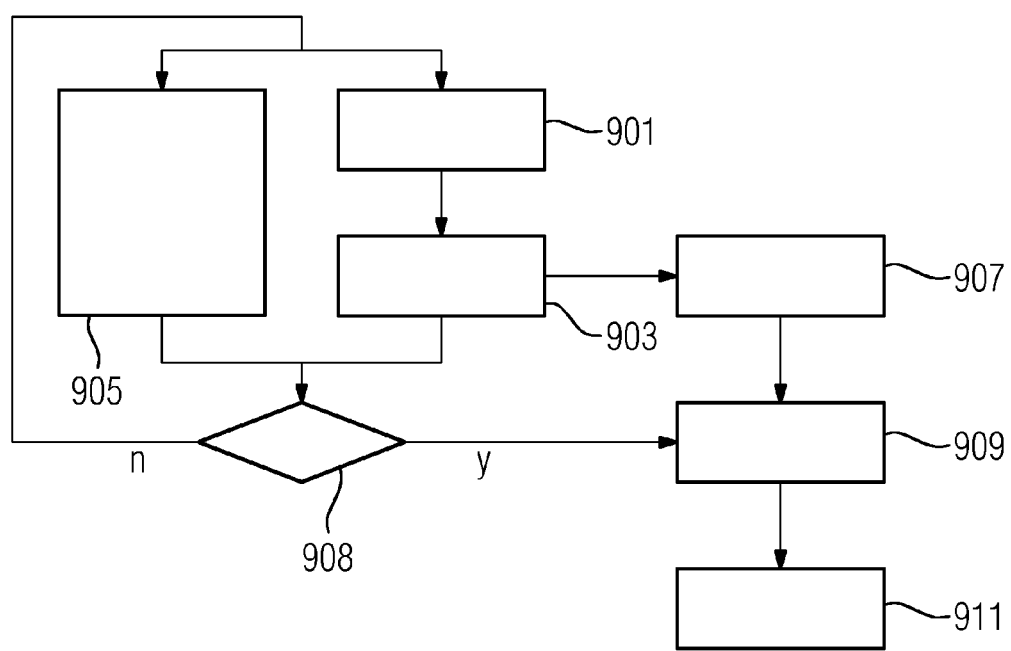

FIG. 9 shows a schematic flow diagram of a method according to the invention for generating magnetic resonance data on the teeth of a patient in a selected region. Here, in the context of a pulse sequence for generating measuring signals, at least one high-frequency pulse, for example an excitation pulse, and optionally one or more refocusing pulses, is irradiated into the selected region which contains the teeth of the patient to be examined (Block 901). The measuring signals generated are read out (Block 903). During the irradiation of the at least one high-frequency pulse (Block 901) and the reading-out of the measuring signals (903), gradient fields for spatial encoding and optionally for generating the desired measuring signals are switched, wherein the irradiated gradient fields at least partially generated by means of a gradient system according to the invention, described in more detail in FIG. 8 so that at least one of the gradient fields in space is not unique. The read-out measuring signals are stored (907) as magnetic resonance data for example in a control mechanism of the magnetic resonance system used. Optionally, the blocks 901 to 907 are repeated, for example with different spatial encoding gradients until a desired number of magnetic resonance data items have been read out of the selected region and stored. To this end, an interrogation 908 can ask whether sufficient magnetic resonance data has already been received ("y") which results in further processing of the magnetic resonance data or not ("n"), which results in a repetition of the steps 901 to 908.

The magnetic resonance data obtained is processed to form an image data set (909), which is, for example, displayed on a terminal of the magnetic resonance system and/or stored in the control mechanism of the magnetic resonance system (911).

The invention claimed is:

1. A gradient system of a magnetic resonance system comprising:
    a gradient coil which generates three superimposed gradient fields in a coordinate system,
    wherein at least one of the three gradient fields extends in parallel or orthogonally to an approximately U-shaped center plane of the teeth of a jaw of a patient,
    wherein the at least one of the gradient fields is not spatially unique in a respective direction of the coordinate system, and
    wherein the at least one of the gradient fields has the same field strength for at least two different coordinate areas in the respective direction.

2. The gradient system as claimed in claim 1, wherein the gradient coil is embodied to be arranged in a measurement volume of the magnetic resonance system around the head of the patient around the jaw of the patient.

3. The gradient system as claimed in claim 1, wherein the gradient system is configured to be fixed on the head of the patient.

4. The gradient system as claimed in claim 3, comprising:
    a biting apparatus,
    wherein the gradient system is configured to be fixed on the head of the patient via the biting apparatus on which the patient bites to achieve fixation.

5. The gradient system as claimed in claim 1, comprising:
    a plurality of high-frequency antennas.

6. The gradient system as claimed in claim 5,
    wherein the gradient coil is arranged around the jaw of the patient, and
    wherein at least one of the plurality of high-frequency antennas is arranged between the gradient coil and the jaw of the patient.

7. The gradient system as claimed in claim 5, wherein at least one of the plurality of high-frequency antennas is arranged intraorally in the interior of the jaw of the patient.

8. A method for generating magnetic resonance data on the teeth of a patient in a selected region using a magnetic resonance system comprising:
    providing irradiation of at least one high-frequency pulse into the selected region,
    reading out measuring signals generated,
    during the irradiation of the at least one high-frequency pulse and the reading-out of the measuring signals, switching three superimposed gradient fields for spatial encoding, wherein the three superimposed irradiated gradient fields are at least partially generated by a gradient coil in a coordinate system, wherein at least one of the three gradient fields extends in parallel or orthogonally to an approximately U-shaped center plane of the teeth of a jaw of the patient, wherein at least one of the gradient fields is not spatially unique in a respective direction of the coordinate system, and wherein the at least one of the gradient fields has the same field strength for at least two different coordinate areas in the respective direction;
    storing the read-out measuring signals as magnetic resonance data;
    processing the magnetic resonance data obtained to form an image data set; and
    displaying and/or storing the image data set obtained from the processing of the magnetic resonance data.

9. A magnetic resonance system for acquiring magnetic resonance data in a selected region within an object under examination, comprising:
    a basic magnet;
    a gradient system comprising a gradient coil configured to generate three superimposed gradient fields in a coordinate system, wherein at least one of the three gradient fields extends in parallel or orthogonally to an approximately U-shaped center plane of the teeth of a jaw of a patient, wherein at least one of the gradient fields is not spatially unique in a respective direction of the coordinate system, and wherein the at least one of the gradient fields has the same field strength for at least two different coordinate areas in the respective direction, a high frequency antenna for receiving the measuring signals;

a control mechanism configured to control the gradient system for evaluating the measuring signals and for creating the magnetic resonance data.

10. The magnetic resonance system as claimed in claim 9, wherein the magnetic resonance system irradiates at least one high-frequency pulse into the selected region of the teeth of the patient, reads out generated measuring signals, during the irradiation of the at least one high-frequency pulse and the reading-out of the measuring signals, switches the gradient fields for spatial encoding, stores the read-out measuring signals as magnetic resonance data, processes the magnetic resonance data acquired to form an image data set and displays and/or stores the image data set obtained from the processing of the magnetic resonance data.

11. A non-transitory computer readable medium comprising:
instructions executable by a computer for generating magnetic resonance data on the teeth of a patient in a selected region using a magnetic resonance system comprising:
providing irradiation of at least one high-frequency pulse into the selected region,
reading out measuring signals generated,
during the irradiation of the at least one high-frequency pulse and the reading-out of the measuring signals, switching gradient fields for spatial encoding, wherein the irradiated gradient fields are at least partially generated by a gradient system in a coordinate system, wherein at least one of the gradient fields is not spatially unique in a respective direction of the coordinate system, and wherein the at least one of the gradient fields has the same field strength for at least two different coordinate areas in the respective direction;
storing the read-out measuring signals as magnetic resonance data;
processing the magnetic resonance data obtained to form an image data set; and
displaying and/or storing the image data set obtained from the processing of the magnetic resonance data.

* * * * *